(12) United States Patent
Zander et al.

(10) Patent No.: US 7,168,563 B2
(45) Date of Patent: Jan. 30, 2007

(54) DISPENSING AID FOR FACILITATING REMOVAL OF INDIVIDUAL PRODUCTS FROM A COMPRESSED PACKAGE

(75) Inventors: Teresa Marie Zander, Bonduel, WI (US); Scott Leslie Williams, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 263 days.

(21) Appl. No.: 10/984,276

(22) Filed: Nov. 8, 2004

(65) Prior Publication Data

US 2006/0096879 A1 May 11, 2006

(51) Int. Cl.
B65D 73/00 (2006.01)
(52) U.S. Cl. ...................... 206/440; 206/494
(58) Field of Classification Search .............. 206/438, 206/440, 499, 494, 812; 604/385.01, 385.02, 604/385.201; 221/45, 56
See application file for complete search history.

(56) References Cited

U.S. PATENT DOCUMENTS

| | | | | |
|---|---|---|---|---|
| 3,338,019 | A * | 8/1967 | Trewella et al. | 206/440 |
| 4,624,365 | A * | 11/1986 | Derdyk | 206/554 |
| 4,770,298 | A | 9/1988 | McFarland et al. | |
| 4,897,982 | A | 2/1990 | Day et al. | |
| 5,022,216 | A | 6/1991 | Muckenfuhs et al. | |
| 5,947,302 | A | 9/1999 | Miller | |
| 6,026,957 | A * | 2/2000 | Bauer et al. | 206/494 |
| 6,454,095 | B1 * | 9/2002 | Brisebois et al. | 206/494 |
| 6,708,823 | B2 * | 3/2004 | Cottingham et al. | 206/440 |
| 6,926,149 | B2 * | 8/2005 | Tippey | 206/494 |
| 2003/0115837 | A1 | 6/2003 | Zimmer et al. | |
| 2004/0129592 | A1 | 7/2004 | Otsubo | |
| 2006/0096880 | A1 | 5/2006 | Zander et al. | |

FOREIGN PATENT DOCUMENTS

| | | |
|---|---|---|
| EP | 0 901 361 B1 | 4/2002 |
| JP | 2001-301857 | 10/2001 |
| JP | 2001-301859 | 10/2001 |
| JP | 2003-182747 | 7/2003 |
| WO | WO 97/21409 A1 | 6/1997 |
| WO | WO 2002/085277 A2 | 10/2002 |

OTHER PUBLICATIONS

American Society for Testing Materials (ASTM) Designation: D1894-01, "Standard Test Method for Static and Kinetic Coefficients of Friction of Plastic Film and Sheeting," pp. 1-6, published Jun. 2001.

* cited by examiner

Primary Examiner—Luan K. Bui
(74) Attorney, Agent, or Firm—Thomas J. Connelly

(57) ABSTRACT

A dispensing aid is disclosed for facilitating removal of an individual product from a compressed package. The compressed package has multiple sides and contains a plurality of compressed products arranged in a row. Each of the products has first and second major surfaces. An opening is formed in the compressed package and is aligned perpendicular to the first major surface of at least one of the products. The opening is sized to allow the products to be individually withdrawn. A sheath is sized to contain one of the products to be withdrawn from the compressed package. The sheath to an adjacent sheath has an average coefficient of friction value which is lower than the average coefficient of friction value of a first product to an adjacent product. The sheath functions to reduce the force needed to remove the contained product from the compressed package.

21 Claims, 4 Drawing Sheets

DISPENSING AID FOR FACILITATING REMOVAL OF INDIVIDUAL PRODUCTS FROM A COMPRESSED PACKAGE

BACKGROUND OF THE INVENTION

Today, many manufacturers are using compressed packaging to reduce the overall size of their packages and thereby save money on shipping cost. Compressed packaging also allows more packages to be placed on a store's shelf since each package takes up less space. This is advantageous since more consumers will be able to find their desired products available on the store shelf. One drawback with compressed packaging is that it is sometimes difficult to remove the first few products from the compressed package. This fact is especially true for personal care products that are designed to absorb urine, menses, fecal matters, or other body fluids. Some examples of such personal care products include adult incontinence garments, infant diapers, training pants, feminine pads, sanitary napkins, pantyliners, etc. These products tend to utilize a non-slippery material, such as a non-woven, for the outer cover and such material has a rather high coefficient of friction value. In addition, many of these products have a rather large surface area that contacts adjacent products, which increases the frictional resistance between products. Furthermore, such products are normally arranged in one or more rows within the package, which means that each major surface of a product is compressed against a major surface of an adjacent product. When the opening to the package is present in the top wall, it requires the consumer to pull an individual product perpendicularly outward from the row and a rather large shear force usually has to be overcome in order to remove the first product.

For adult incontinent products in particular, the consumer is usually an older person who may have deteriorating dexterity and strength. Studies have indicated that many elderly people encounter difficulties in removing the first few adult incontinent products from a compressed package.

Now a dispensing aid has been invented which facilitates the individual removal of a product from a compressed package.

SUMMARY OF THE INVENTION

Briefly, this invention relates to a dispensing aid for facilitating removal of an individual product from a compressed package. The compressed package contains a plurality of compressed products arranged in a row. Each of the products has a first major surface and a second major surface. The first and second major surfaces are aligned opposite to one another. The first major surface has an average coefficient of friction value. An opening is formed in one of the walls of the compressed package and is aligned perpendicular to the first major surface of at least one of the products. The opening is of sufficient size to allow the products to be individually withdrawn such that, as a product is removed from the compressed package, the first major surface of the exiting product will move parallel to an adjacent product. A sheath is sized to contain a product to be withdrawn from the compressed package. The sheath to an adjacent sheath has an average coefficient of friction value lower than the average coefficient of friction value of the first major surface of a product to the major surface of an adjacent product. The sheath functions to reduce the force needed to remove the contained product from the compressed package.

DETAILED DESCRIPTION

Figure 1:
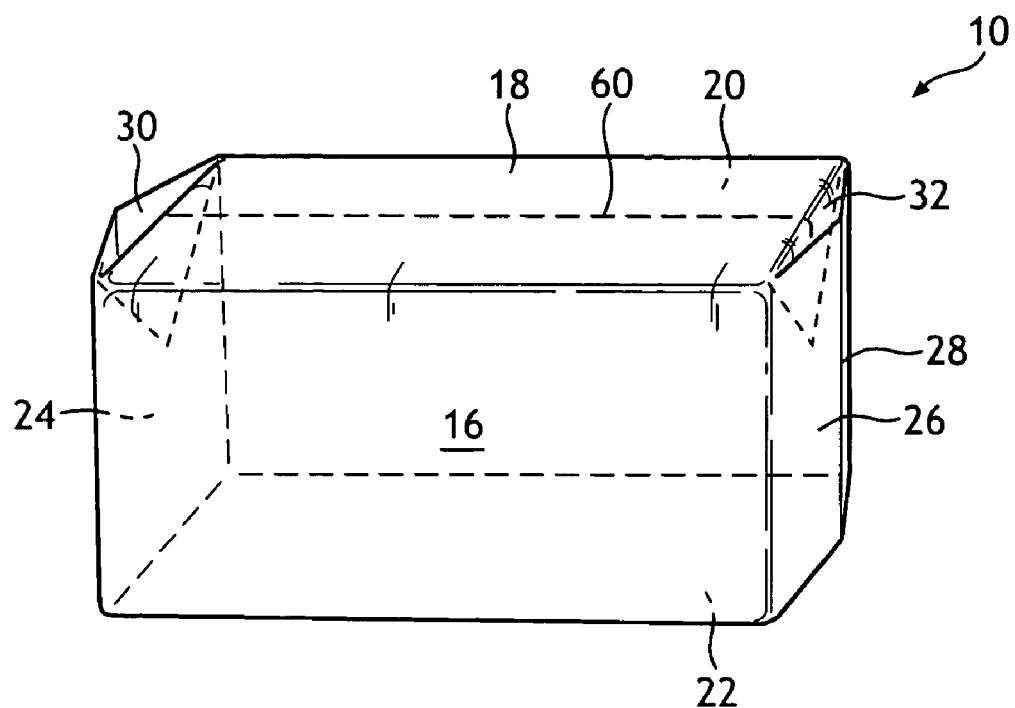
FIG. 1 is a perspective view of a package containing a plurality of compressed products and having a perforation line formed in the top wall which can be broken to form an opening through which the compressed products can be individually removed.
Figure 2:
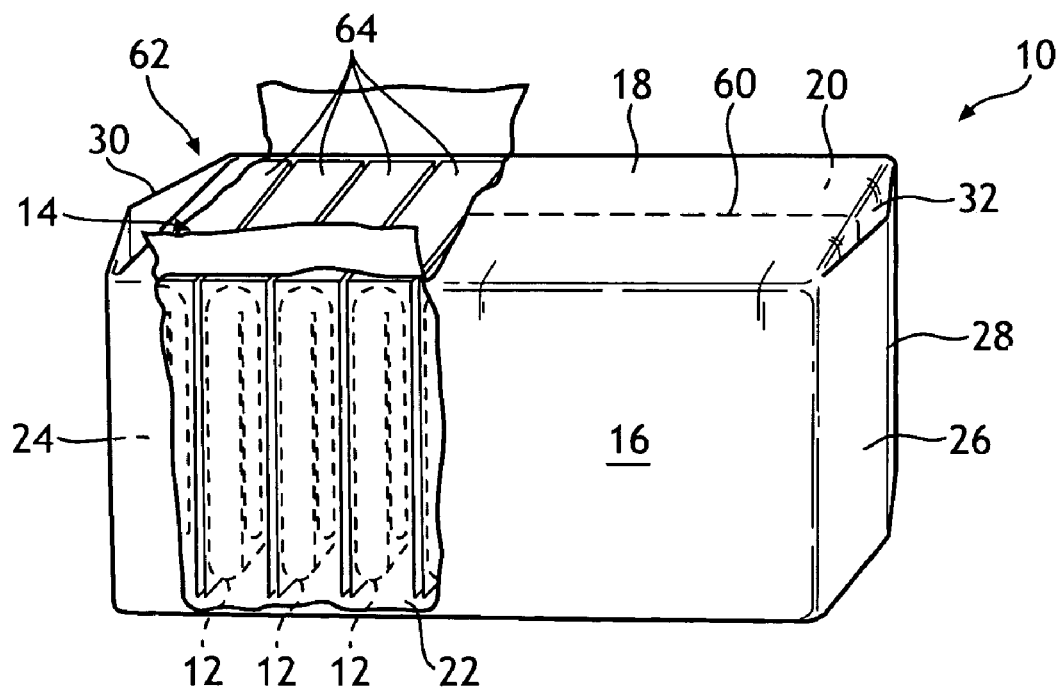
FIG. 2 is a perspective view of the package shown in FIG. 1 with a cut away portion revealing the arrangement of several compressed products contained in sheaths within the package.

Referring to FIGS. 1 and 2, a compressed package 10 is shown containing a plurality of products or articles 12 which are arranged in a row 14, see FIG. 2. One or more rows 14 of products 12 can be enclosed within the compressed package 10. The compressed package 10 has multiple walls and can vary in overall configuration. For example, the compressed package 10 can be configured as a cube having square sides, a rectangle having one or more rectangular sides, a parallelepiped, a cylinder having a circular wall and a pair of end walls, or any other geometrical shape known to those skilled in the packaging art. The dimensions of the compressed package 10 can be adjusted to suit one's needs and requirements. In FIG. 1, the compressed package 10 is depicted as a parallelepiped having six walls, denoted 16, 18, 20, 22, 24 and 26. The six walls include a front wall 16, a top wall 18, a back wall 20, a bottom wall 22, and two side walls 24 and 26.

The compressed package 10 can be formed, constructed or fabricated from a variety of materials. The material should be flexible and pliable and be capable of being compressed, squeezed, deformed, or altered without significantly destroying or tearing the material. Examples of some materials that are capable of being compressed include polymer materials, plastics, thermoplastics, non-wovens, polyesters, and polyolefin films, such as polypropylene and polyethylene, or a laminate thereof. Polymer films have sufficient strength and resistance to creep deformation so as to be ideally suited for making the compressed package 10. Laminates formed from two or more layers of material can also be used. Furthermore, elastomeric materials such as LYCRA, SPANDEX, etc., or other materials known to those skilled in the packaging art, which are capable of being compressed, can also be used to fabricate the compressed package 10. LYCRA and SPANDEX are registered trademarks of E.I. DuPont De Nemours & Co., having an office at 1007 Market Street, Wilmington, Del. 19898.

A polyolefin film that works especially well for making the compressed package 10 is linear low density polyethylene (LLDPE). The linear low density polyethylene (LLDPE) material can have a thickness that ranges from between about 0.5 mils to about 5 mils. Desirably, the linear low density polyethylene (LLDPE) will have a thickness that ranges from between about 1 mil to about 3 mils. More desirably, the linear low density polyethylene (LLDPE) will have a thickness that ranges from between about 1.5 mils to about 2 mils. In general, the thickness of the packaging material is partially dependent upon the types of products 12 being enclosed within the compressed package 10 and the amount of compression force applied to such products 12.

Thermoplastic polymer films facilitate the securement and closure of the compressed package 10 by the application of heat and/or pressure. The compressed package 10 can include seams, pleats, flaps, handles and/or other appendages. Other means of closing and sealing the compressed package 10 include the use of an additional material such as adhesive tape, a cold melt adhesive, a hot melt adhesive, etc. as are known in the packaging art. Once the compressed package 10 is formed, filled with compressed products 12 and sealed, by methods known to those skilled in the art, the compressed package 10 is considered to be unitary. By "unitary" it is meant a compressed package formed of one or more parts that are joined together to form a coordinated entity or a whole unit. For example, a compressed package 10 can be formed from a flexible, polymeric film that is folded, sealed and possibly has another component, such as a closure mechanism, joined thereto.

The unfilled package can be equipped with one or more vent holes (not shown) which will allow air to be removed therefrom while a plurality of compressed products are inserted therein. The filled package is then sealed at its open end to form the compressed package 10.

Normally, a plurality of products 12 are first compressed and then inserted into an unfilled package or cylindrical tube which is open at one end. The filled package or tube is then sealed at its open end to form the compressed package 10. Alternatively, it may also be possible to insert a plurality of uncompressed or partially compressed products into an unfilled package that is open at one end and then seal the open end. The filled and sealed package can then be compressed further to obtain the compressed package 10.

In FIGS. 1 and 2, a seal line 28 is shown formed in the side wall 26. It should be understood that the seal line 28 could be formed in any wall of the compressed package 10, dependent upon the compressed package's overall profile. A pair of gussets, 30 and 32, is formed between the top wall 18 and each of the side walls 24 and 26 of the compressed package 10. Each gusset 30 and 32 is triangular in shape and functions to strengthen the compressed package 10 and can also function to enlarge the opening formed in the compressed package 10 once it is opened. The presence of the gussets 30 and 32 are optional. The opening of the compressed package 10 will be explained in greater detail below.

Still referring to FIG. 1, the compressed package 10 can be subjected to a compression force that squeezes air out of the package 10, the products 12, or both. The amount of compression force exerted on the products 12 before they are inserted into the package, or the amount of compression force exerted on the filled package, can vary depending upon the type of products 12 that is enclosed within the compressed package 10 and the material from which the compressed package 10 is constructed. When the compressed package 10 encloses a plurality of non-breakable products 12, which may contain a certain amount of air, the products 12 are normally compressed before they are inserted into the package. It should be noted that some products are not compressible due to the material from which they are formed. However, disposable absorbent products are ideal products that can be subjected to compression. Desirably, the products 12 are compressed from an initial size to a smaller size by applying a predetermined amount of force, measured in pounds.

Disposable absorbent products refer to absorbent articles which are intended to be worn once by a person and then be discarded. The soiled absorbent products can be land filled or disposed of in an environmentally compatible manner or parts of the absorbent product can be separated out and then be recycled. Disposable absorbent products are not designed to be laundered and reused a number of times like ordinary cotton underwear. The disposable absorbent products are designed to absorb and/or contain one or more body fluids such as urine, perspiration, menses, and other body fluids. Some disposable absorbent products can also absorb exudate in semi-solid or solid form. Some disposable absorbent products, like an adult incontinent undergarment, can be designed to be pulled up or positioned around the torso of a person and will conceal the crotch region. All of the disposable absorbent products function to absorb and/or contain the various body fluids and/or exudate discharged from the human body while being worn about the wearer's crotch region or in a body cavity, such as a tampon.

The term "disposable absorbent products" includes, but is not limited to, adult incontinence garments including pads, briefs and undergarments; infant diapers; child training pants; menstrual pants; feminine care pads and pantyliners; sanitary napkins; tampons; interlabial products; etc. Disposable absorbent products are considered non-breakable products 12 that can be compressed.

A disposable absorbent product may consist of several different layers of material and air is usually present in the product. Therefore, a disposable absorbent product is well adapted to be compressed. In a compressed package of disposable absorbent products 12, the compression forces are normally applied perpendicular to the two side walls 24 and 26 such that the entire row 14 of products 12 are squeezed and made shorter in length. Although the direction at which the compression forces are applied can vary, one should consider the shape and construction of the products 12, so that the products 12 are not materially deformed or rendered useless after being compressed.

By "compressed package" it is meant a package that contains a plurality of products wherein the plurality of products have a pre-insertion dimension, measured along at least one axis, which is greater in length than when the plurality of products are contained in the package. For example, if fourteen products are assembled into a row having a pre-insertion dimension, measured along an axis, say the x axis, of 10 inches (254 mm) and the row of products are then compressed by a force of at least 1 pound to a dimension of less than 10 inches (254 mm) when they are contained in the package, then the products are considered to be contained in a compressed package for purposes of this invention.

The compression force applied to form the compressed package 10 can range from between about 1 pound (lb) to about several thousand lbs. Desirably, the compression force applied to form the compressed package 10 will range from between about 5 lbs to about 1,000 lbs. More desirably, the compression force applied to form the compressed package 10 will range from between about 6 lbs to about 500 lbs. Still more desirably, the compression force applied to form the compressed package 10 will range from between about 7 lbs to about 100 lbs.

Figure 3:
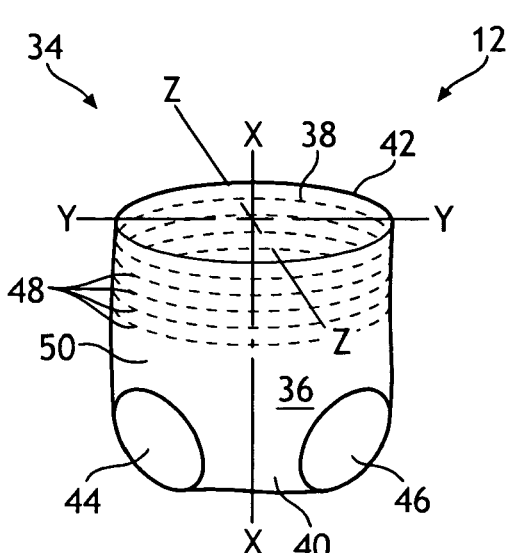
FIG. 3 is a perspective view of an adult incontinent garment having a waist opening and a pair of leg openings which is designed to be pulled up around a user's torso similar to regular cloth underwear.

Referring now to FIG. 3, an example of a product 12 in the form of a disposable absorbent, adult incontinent undergarment 34 is depicted. It should be understood that a wide variety of products 12, each having a different profile, shape, configuration, size and use, and which may be formed from a variety of different materials, can be enclosed within the compressed package 10. The adult incontinent undergarment 34 is simply an illustration of one such product. In FIG. 3, the adult incontinent undergarment 34 is depicted as an integral, tubular shaped product having a front portion 36, a back portion 38 and a crotch portion 40 joined to both the front and back portions, 36 and 38 respectively. The adult incontinent undergarment 34 also has a longitudinal axis X—X, a transverse axis Y—Y, and a vertical Z—Z. The adult incontinent undergarment 34 further has a waist opening 42 and a pair of leg openings 44 and 46. The adult incontinent undergarment 34 can also contain a number of elastic strands 48 situated in the front and back portions, 36 and 38 respectively, which function to allow the adult incontinent undergarment 34 to snugly fit around a wearer's torso.

The adult incontinent undergarment 34 further contains an absorbent pad (not shown) which is positioned within the crotch portion 40 and which can extend into both of the front and back portions, 36 and 38 respectively. The absorbent pad is capable of absorbing body fluids, such as urine, menses, etc., as well as fecal matter. A liquid-impermeable layer (also not shown) is positioned adjacent to the outer surface of the absorbent pad, away from the body of the wearer, and is designed to restrict body fluid from penetrating or passing therethrough. The liquid-impermeable layer will prevent body fluid that has insulted the absorbent pad from contacting and soiling the outer surface of the adult incontinent undergarment 34. If the body fluid is prevented from leaking to the outer surface of the adult incontinent undergarment 34, then it will be kept away from the exterior clothing of the wearer.

Most disposable absorbent products, including the adult incontinent undergarment 34, can utilize either a liquid permeable or a liquid-impermeable outer cover 50. The outer cover 50 can also be breathable, if desired. The outer cover 50 is normally present in the front portion 36, the back portion 38 and the crotch portion 40 of the undergarment 34. The outer cover 50 can be formed from natural or synthetic fibers and usually has a soft feel so as to not chafe the inner thighs of the wearer. The outer cover 50 can be formed from spunbond or from bonded carded webs. An example of a spunbond that works well in disposable absorbent products is a liquid-impermeable, breathable spunbond thermal laminate (BSTL) having a basis weight of 1 ounce per square yard (osy). "BSTL" is a material that is manufactured and commercially sold by Kimberly-Clark Corporation having an office at 401 North Lake Street, Neenah, Wis. 54956. Bonded carded webs are also commercially available and are sold by a number of different vendors.

The outer cover 50 of the adult incontinent undergarment 34 normally has a relatively high, average coefficient of friction value. By "relatively high, average coefficient of friction value" it is meant a coefficient of friction value in excess of about 1. The average coefficient of friction value for a material can be measured by using the American Standard Test Method ASTM 4468, dated Sep. 16, 1998, with slight variations which are explained below, under the heading "COF Test". Coefficient of friction value of the outer cover 50 and the amount of compression force used to compress the products 12 determines how difficult it is to withdraw the first product 12 from the opened compressed package 10.

Figure 4:
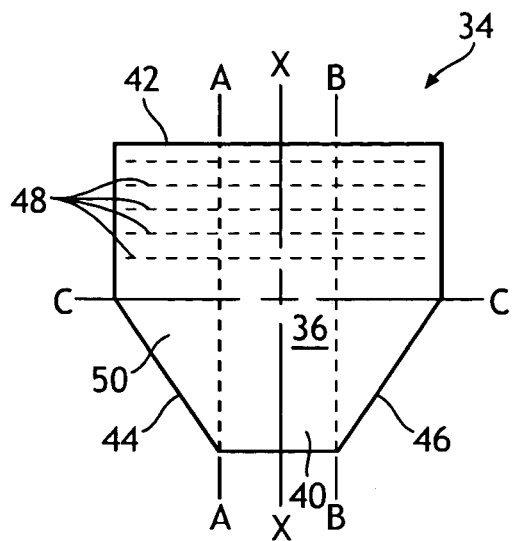
FIG. 4 is a front view of the adult incontinent garment shown in FIG. 3 after it has been flattened in the z direction.
Figure 5:
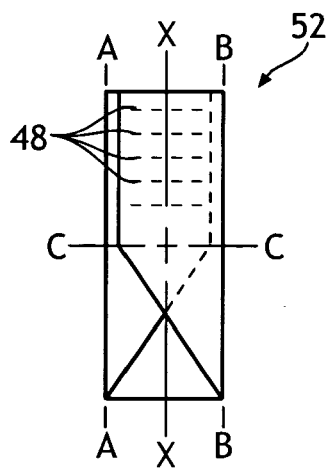
FIG. 5 is a front view of the adult incontinent garment shown in FIG. 4 after the two side portions have been folded along lines A—A and B—B, respectively, over the longitudinal centerline X—X.
Figure 6:
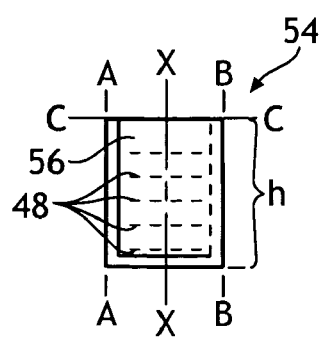
FIG. 6 is a front view of the adult incontinent garment shown in FIG. 5 after the upper half of the adult incontinent garment has been folded down along transverse line C—C over the lower half of the adult incontinent garment.

Turning now to FIGS. 4–6, the adult incontinent undergarment 34 is depicted as being flattened and folded into a configuration wherein it can be arranged into one or more rows, be compressed and then inserted into an open end of a package. In FIG. 4, a plane view of the adult incontinent undergarment 34 is shown wherein the tubular product 34 is flattened with the front portion 36 contacting and resting upon the back portion 38, see FIG. 3. This flattened product 34 is depicted as having two longitudinal fold lines A—A and B—B each located a predetermined distance away from the longitudinal axis X—X. The fold lines A—A and B—B can be arbitrarily selected depending upon the size and shape of the adult incontinent undergarment 34. It should be noted that for smaller products, such as sanitary napkins, adult incontinent pads, pantyliners, etc., the products do not have to be folded before they are inserted into a package. The portion of the adult incontinent undergarment 34 located to the left of the fold line A—A is first folded upon the center portion of the undergarment 34 and then the portion of the adult incontinent undergarment 34 located to the right of the fold line B—B is folded over the first folded portion to arrive at a narrow profile 52, depicted in FIG. 5. This narrow profile 52 is then transversely folded approximately in half along a transverse fold line C—C to arrive at a compacted profile 54, depicted in FIG. 6, having a height h.

Figure 7:
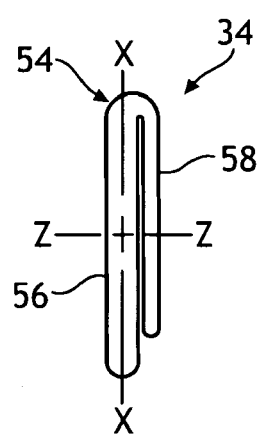
FIG. 7 is an end view of the folded adult incontinent garment shown in FIG. 6.

Referring now to FIG. 7, an end view of the compacted profile 54 is depicted showing the adult incontinent undergarment 34 having a first major surface 56 and a second major surface 58. The first major surface 56 is aligned opposite to the second major surface 58. In addition, the first major surface 56 has a predetermined average coefficient of friction value. The second major surface 58 also has an average coefficient of friction value that can be approximately equal to the average coefficient of friction value of the first major surface 56. Alternatively, the second major surface 58 can have an average coefficient of friction value that is less than or greater than the average coefficient of friction value of the first major surface 56. Stated another way, the first and second major surfaces, 56 and 58 respectively, do not have to have identical or similar average coefficient of friction values, but most likely will. One reason that the first and second surfaces, 56 and 58 respectively, can have a different average coefficient of friction value even though they are constructed from the same material is that one surface can contain a number of rugosities or wrinkles. Such rugosities or wrinkles can equate in a higher average coefficient of friction value.

Still referring to FIG. 7, the first and second major surfaces, 56 and 58 respectively, do not require a particular minimum surface area. However, the surface area of the first and second major surfaces, 56 and 58 respectively, can range from between about 5 square inches (about 3,226 millimeters ($mm^2$)) to about 100 square inches (about 64,516 $mm^2$). For example, a small/medium size DEPEND adult incontinent undergarment when folded into the compacted profile 54, has a width w of about 5 inches (about 127 mm) and a length l of about 8 inches (about 203 mm). DEPEND is a registered trademark of Kimberly-Clark Corporation having an office at 401 North Lake Street, Neenah, Wis. 54956. A large size DEPEND adult incontinent undergarment would have slightly larger width w and length l dimensions.

Returning again to FIGS. 1 and 2, the compressed package 10 contains a perforation line 60 formed in the top wall 18. The perforation line 60 extends completely across the length of the top wall 18 and extends down a portion of each of the side walls 24 and 26. The perforation line 60 is shown being located an equal distance between the front and back walls, 16 and 20 respectively, but could be aligned closer to the front wall 16, if desired. The perforation line 60 is designed to be easily broken when the consumer pulls on the package material located at the upper edges adjacent to the junction of the front wall 16 with the top wall 18 and at the junction formed by the back wall 20 and the top wall 18. This pulling action will cause the perforation line 60 to break and form an opening 62 into the compressed package 10, see FIG. 2. The opening 62 is shown being aligned perpendicular to the first major surface 56 of at least one of the products 12. Desirably, the opening 62 will be aligned perpendicular to the first and second major surfaces, 56 and 58 respectively, of a majority of the products 12. More desirably, the opening 62 will be aligned perpendicular to the first and second major surfaces, 56 and 58 respectively, of all of the products 12.

It should be noted that other ways of forming an opening 62 into the compressed package 10 can also be utilized.

The opening 62 should be of sufficient size to allow the products 12 to be individually withdrawn such that as a product 12 is removed from the compressed package 10, the first major surface 56 of an exiting product will move parallel to an adjacent product 12. Desirably, the first and second major surfaces, 56 and 58 respectively, of an exiting product 12 will move parallel to a major surface of each adjacent product 12.

Figure 8:
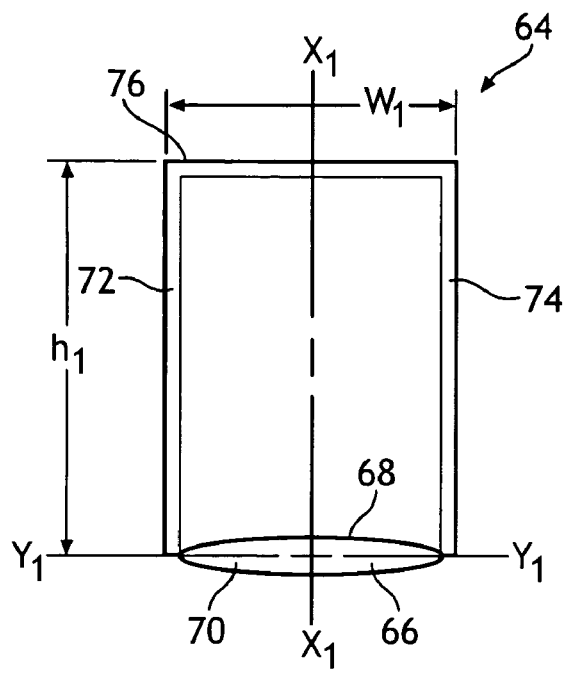
FIG. 8 is a perspective view of a sheath formed from two pieces of material joined together and having an open end.
Figure 9:
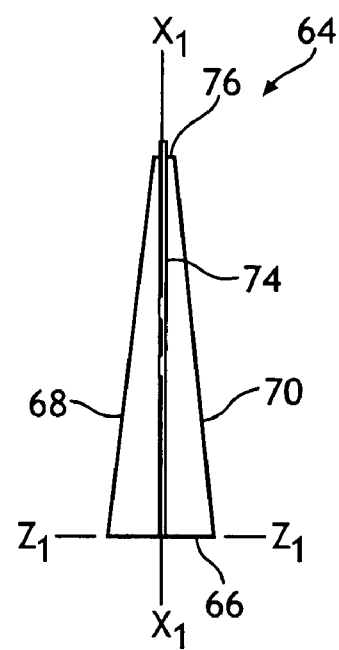
FIG. 9 is a right side view of the sheath shown in FIG. 9.

Referring now to FIGS. 8 and 9, the dispensing aid of this invention includes at least one sheath 64 having an open end 66 and being sized to contain one of the products 12 to be withdrawn from the compressed package 10. By "sheath" it is meant a case having an enveloping structure, such as a tubular sleeve closed at one end. The sheath 64 is capable of at least partially enclosing, containing or encasing a product 12. Desirably, the sheath 64 is sized so as to completely contain or enclose a product 12. The sheath 64 is shown having a height $h_1$ and a width $w_1$. The sheath 64 also has a longitudinal axis $X_1$—$X_1$, a transverse axis $Y_1$—$Y_1$, and a vertical axis $Z_1$—$Z_1$. The sheath 64 should be formed from a pliable and flexible material and can be viewed as being similar to a knife sheath in that it functions to contain a product 12. The sheath 64 can be formed from one or more pieces of material which are joined or bonded together to form a tubular or conical sleeve that has an open end 66.

In FIGS. 8 and 9, the sheath 64 is depicted as being formed from two separate pieces of material 68 and 70 having similar or identical configurations and dimensions. The two pieces of material, 68 and 70, are joined together by side seams 72 and 74 and by an end seam 76. Alternatively, a single sheet of material can be folded upon itself and be seamed at the two sides to form a similar structure. The side seams 72 and 74 and the end seam 76 can be formed using any joining means known to one skilled in the art. Examples of some ways to form the side seams 72 and 74 and the end seam 76 include, but are not limited to, the use of an adhesive, using heat, using pressure, using heat and pressure, using sonic energy, using ultrasonic energy, using a mechanical fastener, using thread which stitches the two pieces of material 68 and 70 together, etc. The exact type of seam that is formed will depend upon the material from which the two pieces of material 68 and 70 are composed.

The test procedure used for calculating the average coefficient of friction (COF) values for the outer cover 50 and for each of the three different size sheaths 64, 64' and 64" to an adjacent sheath interface will now be discussed.

COF Test

A test was conducted to obtain the average coefficient of friction (COF) values for surfaces in contact within the package 10 (product 12 to product 12 and product 12 to sheath 64). Testing was first conducted without the presence of the sheath 64. Additional testing was then conducted with the sheath 64 added between the products 12. The results of the average coefficient of friction tests are displayed graphically in Chart 1. It should be noted that this average coefficient of friction test represents only one way to determine the average coefficient of friction values. Other tests known to those skilled in the art can also be used to determine the average coefficient of friction values.

The longitudinal axes $x_1$—$x_1$ of each of the pair of sheaths 64 was axially aligned with the longitudinal axis x—x of the selected products 12. The selected products 12 was folded into the configuration shown in FIG. 7. The testing was conducted in a standard laboratory atmosphere of 23°±1° Celsius (73.4° Fahrenheit (F)±1.8° F.) and 50%±2% Relative Humidity.

The following equipment was utilized:
1. A Syntech S/1 from: MTS System Corp., P.O. Box 12226, Research Triangle Park, N.C. 27709-4226.
2. A 100 Newton (9.98 kg/22 lb) load cell.
3. Clip mounting board with attached pulley wheel, Kimberly-Clark Corporation's item number 1096212.
4. Standard Cable attached to Syntech grip on one side and a skid resistant clip on other. Kimberly-Clark Corporation's item number 1096212.
5. Standard extension insert.
6. 6"×10" acrylic platen with weights equivalent to 3,640 grams or approximately 8 lbs.
7. Basic coefficient of friction software package (kinetic coefficient of friction results required).
   a. Kinetic Formula $\mu_k = A_k/B$
      i. $A_k$=the average gram value obtained during the 60 second test time (6" of travel)
      ii. B=6×10 acrylic platen and weights total weight.

The test methodology was as follows:

Specimen and Equipment Preparation
1. Twenty-five film sheaths were used to fully sheath each product. All twenty-five sheaths measured 250 mm×200 mm. Each sheath was sealed on three sides. The open end of each sheath was not closed or sealed.
2. One product was placed within each sheath. Five sheathed stacks of five individual products were utilized. The products within each of the stacks were initially compressed 40%, by the use of 8 pounds of weights from an original stack height of about 176 mm down to a stack height of about 106 mm, 100%−(106/176)%=40%.
3. Attach a standard cable to the top arm extension insert.
4. Start with a stack of five sheathed products. Place stack on end of clip mounting board. Next, attach skid resistant clip to the number 3 product. Make sure the cable is taut. Final sample prep for test specimen is to add acrylic platen and weights to top of stack.
5. The stack of five products was manually held stationary so that only the number 3 product could move.

Testing Procedure
1. The Syntech tester was activated such that the top arm began to move upward at a speed of 6.00 in/min.
2. Once the selected product was completely removed from the row of products, the upward movement of the top arm was stopped.
3. The kinetic coefficient of friction result was recorded using the formula listed above in item #7.
4. Repeat steps 1–3 on the four remaining compressed stacks having the same size slip sheets and average the five recorded values in order to obtain a kinetic, average coefficient of friction result.
5. Repeat the above test procedure on the two remaining groups of five compressed stacks.
6. Chart the kinetic, average coefficient of friction values to obtain a chart.

Each of the sheaths to an adjacent sheath has an average coefficient of friction value that is at least 2 times less than the average coefficient of friction value of a first product to an adjacent product. More desirably, each of the sheaths to an adjacent sheath has an average coefficient of friction value that is at least 2.5 times less than the average coefficient of friction value of a first product to an adjacent product. Even more desirably, each of the sheaths to an adjacent sheath has an average coefficient of friction value that is at least 3 times less than the average coefficient of friction value of a first product to an adjacent product.

The sheath 64 should be formed from a material that exhibits a relatively low, average coefficient of friction value when compressed between the products. By "a relatively low, average coefficient of friction value" it is meant an average coefficient of friction value of less than about 1. The average coefficient of friction value for the sheath 64 can be measured using the same American Standard Test Method ASTM 5653 dated Apr. 6, 2004, with slight variations which were explained under the heading "COF Test". Typically, the sheath 64 will have an average coefficient of friction value of from between about 0.2 to about 1. Stated another way, each sheath 64 should have an average coefficient of friction value that is at least 10% less than the average coefficient of friction value of the first major surface 56 of the product 12.

Desirably, each of the sheaths 64 will have an average coefficient of friction value of from about 0.2 to about 0.8. More desirably, each of the sheaths 64 will have an average coefficient of friction value of from about 0.2 to about 0.76. Even more desirably, each of the sheaths 64 will have an average coefficient of friction value of from about 0.2 to about 0.7. Stated another way, each of the sheaths 64 should have an average coefficient of friction value that is less than the average coefficient of friction value of the first major surface 56 of the first product 66. Desirably, each of the sheaths 64 should have an average coefficient of friction value that is at least 0.2 less than the average coefficient of friction value of the first major surface 56 of the first product 66. More desirably, each of the sheaths 64 should have an average coefficient of friction value that is at least 0.24 lower than the average coefficient of friction value of the first major surface 56 of the first product 66. Even more desirably, each of the sheaths 64 should have an average coefficient of friction value that is at least 0.3 lower than the average coefficient of friction value of the first major surface 56 of the first product 66. This difference will assure that the products 12 can be easily withdrawn from the compressed package 10.

Each sheath 64 can be formed from a polymeric material such as polypropylene or polyethylene. Desirably, the polymeric material is a thin film having a thickness of only a few mills. A thickness of from between 1 mil to about 2 mils works well. More desirably, each of the sheaths 64 can be formed from a low density polymeric film such as low density polypropylene or low density polyethylene. The sheaths 64 can be formed using a blown film method or a cast film method. Blown films can be manufactured with a lower, average coefficient of friction value relative to cast films. The average coefficient of friction value for a blown film, for this application, should range from between about 0.1 to about 0.5. One supplier of blown films is the Bemis Company, Inc., having an office at 222 South Ninth Street, Suite 2300, Minneapolis, Minn. 55402-4099. The average coefficient of friction value for a cast film, for this application, should range from between about 0.5 to about 0.8. A supplier of a cast film is Pliant Corporation, having an office at 1475 Woodfield Road, Suite 700, Schaumburg, Ill. 60173.

As mentioned above, each compressed package 10 can contain a plurality of products 12 and each product 12 can be contained in a sheath 64. However, it may not be necessary to enclose each product 12 in a sheath 64 because after several products 12 have been removed from the compressed package 10, the remaining products 12 will be loosely constrained thereby making it easy for the consumer to withdraw additional products 12. For this reason, only the first few products 12 to be withdrawn from the compressed package 10 need to be individually contained in a sheath 64. Desirably, at least 25% of the products 12 in the compressed package 10 are individually contained in a sheath 64. More desirably, at least 50% of the products 12 in the compressed package 10 are individually contained in a sheath 64. Most desirably, from about 50% to about 100% of the products 12 in the compressed package 10 are individually contained in a sheath 64.

Alternatively, every other product 12 within the compressed package 10 could be contained in a sheath 64. This would provide a sheath 64 against each adjacent product 12 thereby lowering the coefficient of friction needed to remove a product 12 from the compressed package 10 and cutting the cost of the sheaths 64 in half.

The minimum number of sheaths 64 needed to facilitate withdrawal of the first product 66 from the row 14 of products 12 enclosed within the compressed package 10 is one. The maximum number of sheaths 64 which can be used in the compressed package 10 is equal to the number of products 12 contained in the compressed package 10. For example, if there are fifteen products 12 in the compressed package 10, then fifteen sheaths 64 would be utilized.

The profile or configuration of an individual sheath 64 can vary. For example, the sheath 64 can have a square, rectangular, triangular, polygonal, hexagonal, circular, round, oval, elliptical or some other geometrical shape. A square or rectangular shape works well because material is usually supplied as an elongated strip, rolled up into a supply roll. When the elongated strip is cut into smaller pieces, little or no waste is encountered when a square or rectangular profile is the finished form. The sheath 64 can be narrower, wider, shorter or longer than the first major surface 56 of the product 12. Since the first major surface 56 of the product 12 is typically folded into a rectangular shape as depicted in FIG. 6, it makes sense from a manufacturing standpoint to form the sheath 64 into a rectangular shape as well.

The compressed package 10 can have one or more rows 14 of products 12. The number of products 12 making up each row 14 can vary. For example, the total number of products 12 in a given row 14 can be from between 2 to about 500 products. Desirably, each row 14 of products 12 will contain from between about 3 to about 200 products. More desirably, each row 14 of products 12 will contain from between about 5 to about 100 products. Still more desirably, each row 14 of products 12 will contain from between about 10 to about 25 products.

For a compressed package 10 containing fifteen products 12 in a single row 14, the number of sheaths 64 that can be included in the compressed package 10 can range from between one to fifteen. The exact number of sheaths 64 utilized will depend upon the desire of the manufacturer. One sheath 64 is needed to ensure that the first product 12 is easily removed, especially when that first product 12 is located in the middle portion of the row 14. Once the first product 12 is removed from the compressed package 10, the force needed to remove each subsequent product 12 should diminish since additional space will be present in the compressed package 10. However, depending on how tightly the products 12 were initially compressed, after removing the first product 12, it may still be rather difficult to remove the next few products 12. For this reason, the manufacturer may wish to utilize 2, 3, 4, 5, 6 or more sheaths 64.

It should be noted that the use of additional sheaths 64 will increase the overall cost of the finished compressed package 10, and, therefore, a manufacturer will most likely try to economize on the total number of sheaths 64 that are utilized in the compressed package 10. A number of factors will dictate how many sheaths 64 are needed. These factors include: the size of the first and second major surfaces 56 and 58 of the products 12, the average coefficient of friction values between adjacent products 12, the number of products 12 situated in each row 14, the amount of force used to initially compress the products 12, the average coefficient of friction value of each sheath 64, the size and location of the opening 62, etc.

It should also be noted that the first major surface 56 of the first products 12 to be removed from the compressed package 10 has a predetermined surface area. Each of the sheaths 64 can have a surface area that ranges from between about 20% to about 150% of the predetermined surface area of the first major surface 56. Desirably, the surface area of each of the sheaths 64 can range from between about 25% to about 120% of the predetermined surface area of the first major surface 56. More desirably, the surface area of each of the sheaths 64 can range from between about 40% to about 100% of the predetermined surface area of the first major surface 56. Even more desirably, the surface area of each of the sheaths 64 can range from between about 60% to about 100% of the predetermined surface area of the first major surface 56. Most desirably, the surface area of each of the sheaths 64 can range from between about 75% to about 100% of the predetermined surface area of the first major surface 56. It is also not necessary that all of the sheaths 64 have the same dimensions, although, from a manufacturing standpoint, they most likely will.

When the perforation line 60 is formed in the top wall 18, it can be fabricated such that the opening 62 will be created in the central portion of the top wall 18. This means that the manufacturer can individually encase several of the products 12 located in the middle of the row 14 in sheaths 64 so that any one of these several products 12 can be the first product 12 to be removed from the compressed package 10. Once five or six products 12 have been withdrawn from the compressed package 10, the force needed to remove each additional product 12 will be substantially reduced and additional sheaths 64 may no longer be needed.

It should be noted that if the opening 62 is aligned adjacent to an end of the row 14 of products 12, then the end product 12 can be contained in a sheath 64 and several adjacent products 12 can also be contained in a respective sheath 64. Once the first few products 12 have been removed from the compressed package 10, it should be easy for the consumer to withdraw the remaining products 12 which do not have to be individually encased in a sheath 64.

Figure 10:
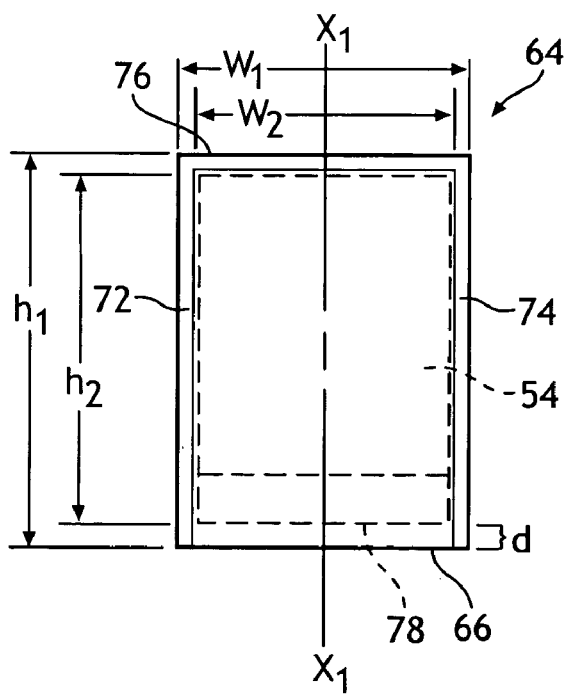
FIG. 10 is a front view of the sheath shown in FIG. 8 having a height $h_1$ that is greater than the height $h_2$ of the contained disposable absorbent product.
Figure 11:
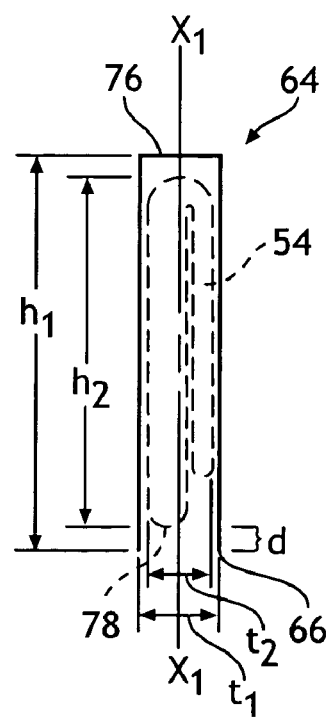
FIG. 11 is a side view of the sheath shown in FIG. 10.

Referring now to FIGS. 10 and 11, a front view of the sheath 64 shown in FIG. 8 is depicted having a height $h_1$, a width $w_1$ and a thickness $t_1$, see FIG. 11. A folded and compacted product 54 is contained within the sheath 64. The folded and compacted product 54 has a height $h_2$, a width $w_2$ and a thickness $t_2$. The height $h_2$, the width $w_2$ and the thickness $t_2$ of the product 54 are less than the height $h_1$, the width $w_1$ and the thickness $t_1$, respectively, of the sheath 64. One will notice that the sheath 64 is closed at the top by the end seam 76 and has the open end 66 located on the bottom. This is the orientation the sheath 64 will have in the closed compressed package 10, see FIG. 2. This orientation allows the consumer to grasp the sheath 64 between his or her thumb and forefinger and remove both the sheath 64 and the product 54 from the compressed package 10. The sheath 64 also is longer than the folded and compacted product 54. The product 54 has an end 78 that is spaced above the open end 66 of the sheath 64 by a distance d. The distance d can range from between about 0.01 inches (about 0.25 millimeters (mm)) to about 1 inch (about 25.4 mm). Alternatively, the sheath 64 can have a height $h_1$ that is approximately equal to or less than the height $h_2$ of the product 54.

Figure 12:
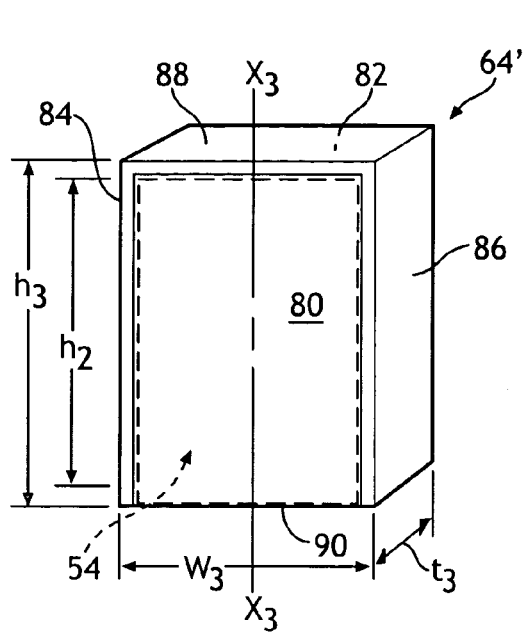
FIG. 12 is a perspective view of an alternative embodiment of a sheath in the shape of a parallelepiped having a height $h_3$, a width $w_3$ and a thickness $t_3$ and containing a disposable absorbent product having a height $h_3$ which is equal to the height $h_3$ of the sheath.
Figure 13:
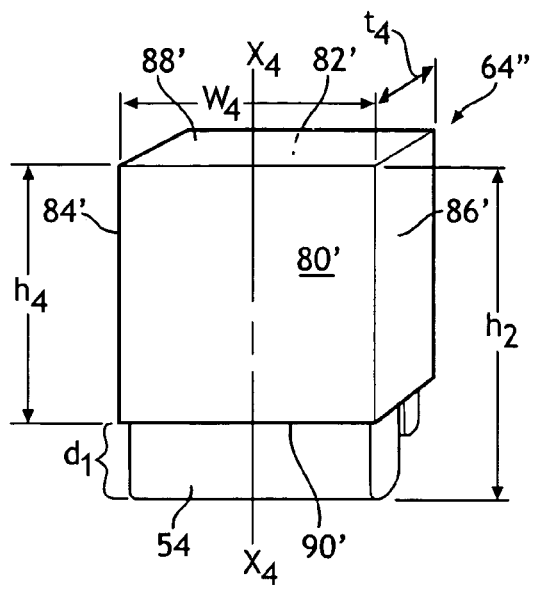
FIG. 13 is a perspective view of a sheath in the shape of a parallelepiped having a height $h_4$, a width $w_4$ and a thickness $t_4$ and containing a disposable absorbent product having a height $h_2$ that is greater than the height $h_4$ of the sheath.

Referring now to FIGS. 12 and 13, two different sizes of an alternative embodiment of a sheath are shown. In FIG. 12, a sheath 64' is depicted having a parallelepiped configuration instead of a tubular or conical design. The sheath 64' has a longitudinal axis $X_3$—$X_3$, a front wall 80, a back wall 82, two side walls 84 and 86 and an end wall 88. An opening 90 is formed in the lower surface of the sheath 64' so that a product 54 can be easily inserted into and be removed from the sheath 64'. This is the orientation the sheath 64' will have in the closed compressed package 10, see FIG. 2. This orientation allows the consumer to grasp the sheath 64' between his or her thumb and forefinger and remove both the sheath 64' and the product 54 from the compressed package 10. The sheath 64' also has a height $h_3$, a width $w_3$ and a thickness $t_3$. The product 54 has a height $h_2$ which is approximately equal to the height $h_3$ of the sheath 64'. Since the first and second major surfaces, 56 and 58 respectively, of the product 54 will usually have a higher, average coefficient of friction than the sheath 64', these surfaces will be less slippery. As the sheath 64' and the product 54 are pulled up out of the row 14 of products 12 housed in the compressed package 10, the sheath 64' will reduce the force needed to withdraw the product 54 from the compressed package 10. The sheath 64' can then be separated from the product 54 so that the product 54 can be positioned adjacent to the consumer's body. The sheath 64' can be used to enclose a soiled disposable absorbent article that has been removed from the consumer's body.

In FIG. 13, a sheath 64" is depicted having a parallelepiped configuration. The sheath 64" has a longitudinal axis $X_4$—$X_4$, a front wall 80', a back wall 82', two side walls 84' and 86' and an end wall 88'. An opening 90' is formed in the sheath 64" so that the folded and compacted, disposable absorbent product 54 can be easily inserted into and be removed from the sheath 64". The sheath 64" also has a height $h_4$, a width $w_4$ and a thickness $t_4$. The product 54, contained in the sheath 64" is below the opening 90' by a distance $d_1$. The distance $d_1$ can range from between about 0.25 inches (about 6.35 millimeters (mm)) to about 2 inches (about 51 mm). More desirably, the distance d, can range from between about 0.35 inches (about 8.9 mm) to about 1.5 inch (about 38 mm). Most desirably, distance d, can range from between about 0.5 inches (about 12.5 mm) to about 1 inch (about 25.4 mm). One reason for making the sheath 64" shorter than the height $h_2$ of the product 54 is to save on the amount of sheath material that is needed, thereby reducing the overall cost of the compressed package 10.

Figure 14:
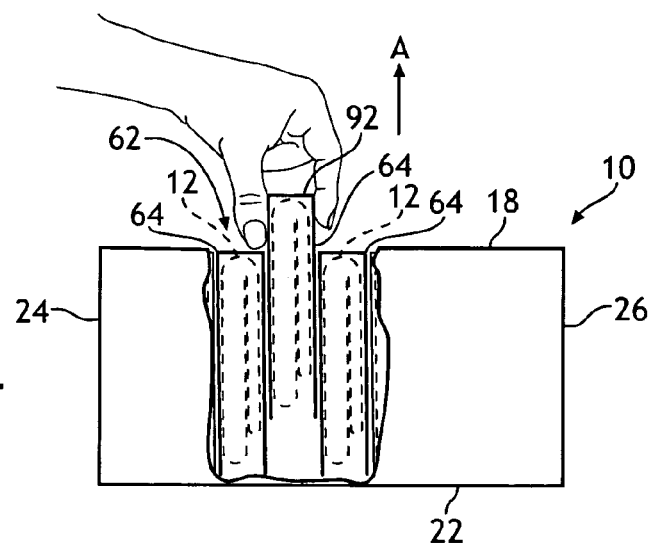
FIG. 14 is a front view of the package shown in FIG. 1 after the perforation line has been broken to form an opening and depicting a consumer pulling an individual compressed product out of the compressed package.

Referring now to FIG. 14, a first product 92 and its surrounding sheath 64 are shown being removed from the compressed package 10 by having the consumer pinch the first product 92 and the sheath 64 between his or her thumb and forefinger. The consumer pulls both the sheath 64 and the first product 92 upward out through the opening 62. Both the first product 92 and the sheath 64 are pulled perpendicularly out from the horizontal row 14 of products 12 at the same time. The first product 92 and the sheath 64 are taken from a middle portion of the row 14. The consumer can grasp the top portion of the sheath 64 and pinch it so that both the first product 92 and the sheath 64 will be removed simultaneously. It should be noted that the plurality of products 12 forming the row 14 were compressed in a horizontal direction between the ends 24 and 26 of the compressed package 10. As the first product 92 and the sheath 64 are removed from the compressed package 10, the first and second major surfaces, 56 and 58 respectively, see FIG. 7, of the first product 92 will move in shear relative to the inside of the sheath 64. In turn, the sheath 64 will move in shear relative to the two adjacent sheaths 64 or will move in shear relative to one of the major surfaces 56 and 58 of the two adjacent products 12, assuming that each adjacent product 12 is not contained in a sheath 64.

Once the first product 92 and the sheath 64 have been withdrawn from the compressed package 10, the first product 92 is removed from its sheath 64. The sheath 64 can be used as a pouch or wrapper for a soiled absorbent product that is being replaced by the first product 92. The disposal feature is very beneficial in that it allows the user to dispose of the soiled product at the time of removal of the soiled product from his or her body or to retain the soiled product in a sanitary fashion until it can be more discretely discarded. The fact that the sheath 64 can be essentially the same size or larger than the first product 92 will ensure that it can house or contain the used soiled product in a sanitary fashion.

It should be noted that if the first product 92 to be withdrawn from the compressed package 10 is located at either end of the row 14 of compressed products 12, then this first product 92 should be contained within a sheath 64. The sheath 64 can be positioned next to or between the 1st, 2nd, 3rd, 4th, 5th, 6th, etc. products 12 to be withdrawn from the compressed package 10. Desirably, at least about 50% of the products 12 in the compressed package 10 are individually contained within a sheath 64. More desirably, at least about 75% of the products 12 in the compressed package 10 are individually contained within a sheath 64. Even more desirably, from between about 75% to about 95% of the products 12 in the compressed package 10 are individually contained within a sheath 64. Most desirably, each product 12 in the compressed package 10 is individually contained within a sheath 64.

Figure 15:
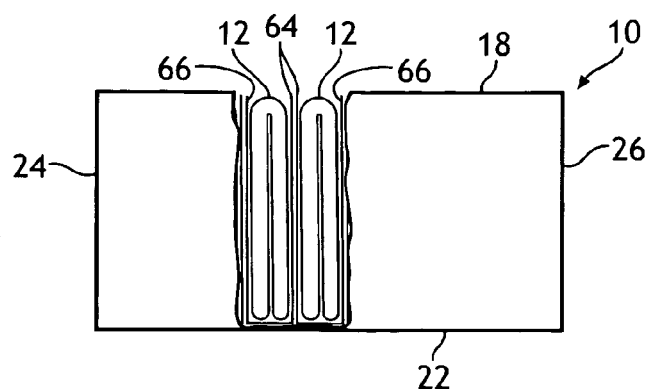
FIG. 15 is a front view of the package shown in FIG. 1 depicting each of the sheaths having an open end at the top surface.

Referring now to FIG. 15, an alternative embodiment is depicted wherein the open end 66 of each of the sheaths 64 is positioned adjacent to the top wall 18 of the package 10. In this configuration, the consumer can simply pinch the product 12 and lift it out of the enclosing sheath 64. If the consumer does not desire to use the sheath 64 to enclose a used product, the sheath 64 can remain in the package 10.

The test procedure used for calculating the average peak load needed to remove a selected product from a compressed package will now be discussed.

Force Test

A test was conducted to record the average peak load in grams (g) needed to remove a selected product 12 contained in a sheath from the middle of a row of fourteen products housed within a compressed package 10. The selected product was the seventh product in the row of fourteen products. The fourteen products were compressed by a weight of 23 lbs. It should be noted that this force test represents only one way to determine the force value necessary to remove the first product from the compressed package. Other means known to those skilled in the art can be used to determine that the sheath(s) actual reduces the force needed to remove the first product from the compressed package.

The longitudinal axes $x_1$—$x_1$ of each of the sheaths 64 was axially aligned with the longitudinal axis x—x of the selected products 12. The selected product was folded into the configuration shown in FIG. 7. The testing was conducted at room temperature, 70° F.

The following equipment was utilized:
1. A Syntech S/1 from: MTS System Corp., P.O. Box 12226, Research Triangle Park, N.C. 27709-4226
2. A 100 N (9.98 kg/22 lb) load cell.
3. Standard jaws with 3-inch (76.2 mm) grip facings.
4. A flat 10-inch (254 mm) diameter circular platen base.
5. Basic tensile software package (Peak Load results required).

The test methodology was as follows:

Specimen Preparation
1. Seventy film sheaths were used to fully sheath each of seventy products. All seventy sheaths measured 250 mm×200 mm. Each sheath was sealed on three sides. The open end of each sheath was not closed or sealed.
2. Five compressed packages, each containing one horizontal row of fourteen compressed absorbent products, were utilized. One product was placed within each sheath. Fourteen sheathed products were initially compressed by 40% from an original length of about 500 mm to a length of about 300 mm. The fourteen products were compressed by a weight of 23 lbs and placed within a film bag to obtain the compressed package. Each compressed package contained a perforation line located in the top wall. The perforation line in each compressed package was torn open by pulling on the material forming the compressed package. This tearing action created an opening in each of the compressed packages.

3. This selected product was the seventh product in the row of fourteen products housed in each of the compressed packages. Seventy products divided by fourteen products per compressed package equals five compressed packages.

Testing Procedure

1. Starting with an opened, compressed package, the packaging material forming the front and back walls of the compressed package was pulled outwardly and downwardly so that the top surface of several of the products located in the mid-section of the row of fourteen products were exposed. The top surfaces of the products located at and near the opposite ends of the row of fourteen compressed products within the compressed package were not completely exposed at this time. At least about 0.25 inches (about 6.0 mm) of a selected product, located in the mid-section as illustrated below, was exposed. The seventh product in the row, counting from one end, is the first or selected product to be removed from the compressed package.
2. Bring the two top jaws of the Syntech tester down onto the mid-section of the selected product to be removed from the compressed package. Clamp the two jaws at least about 0.25 inches (about 0.6 mm) down from the fold line (see FIG. 7) onto the first and second major surfaces of the selected product. Note: the two products located adjacent to the seventh product may be slightly compressed by the edges of the two jaws in order to achieve the appropriate clamping of the selected product.
3. Manually hold down the bottom half of the compressed package so that the compressed package does not move when the two top jaws begin to move upward.
4. Run the test at 1,000 mm/min.
5. Stop test when the selected product is completely removed from the row of products housed in the compressed package.
6. Record the force value of the peak load in grams (g).
7. Repeat the test on the four remaining compressed packages having the same size slip sheets and average the five recorded force values to obtain an average peak load force.
8. Chart the average recorded force values to obtain a chart.

While the invention has been described in conjunction with several specific embodiments, it is to be understood that many alternatives, modifications and variations will be apparent to those skilled in the art in light of the aforegoing description. Accordingly, this invention is intended to embrace all such alternatives, modifications and variations that fall within the spirit and scope of the appended claims.

We claim:

1. A dispensing aid for facilitating removal of an individual product from a compressed package, comprising:
    a) a plurality of products arranged in a row within said compressed package, each of said products having a first major surface and a second major surface, said first major surface aligned opposite to said second major surface, and said first major surface of a product to a major surface of an adjacent product having an average coefficient of friction value;
    b) an opening formed in a wall of said compressed package, said opening being aligned perpendicular to said first major surface of at least one of said products, and said opening being of sufficient size to allow said products to be individually withdrawn such that as a product is removed from said compressed package, said first major surface of an exiting product moves parallel to an adjacent product; and
    c) a sheath having an open end and being sized to contain one of said products to be withdrawn from said compressed package, said sheath to an adjacent sheath having an average coefficient of friction value lower than said average coefficient of friction value of said first major surface of a product to a major surface of an adjacent product, whereby said sheath reduces the force needed to remove said contained product from said compressed package.

2. The dispensing aid of claim 1 wherein said plurality of products contained in said compressed package are compressed by a force of at least 1 pound in at least one direction and said average coefficient of friction value of said sheath to an adjacent sheath is at least two times less than the average coefficient of friction value of said product to an adjacent product.

3. The dispensing aid of claim 1 wherein said average coefficient of friction value of said sheath to an adjacent sheath is at least 2.5 times less than the average coefficient of friction value of said product to an adjacent product.

4. The dispensing aid of claim 3 wherein said average coefficient of friction value of said sheath to an adjacent sheath is at least three times less than the average coefficient of friction value of said product to an adjacent product.

5. The dispensing aid of claim 1 wherein at least one of said products within said compressed package is contained in a sheath that is open at the bottom.

6. The dispensing aid of claim 1 wherein at least one of said products within said compressed package is contained in a sheath that is open at the top.

7. The dispensing aid of claim 1 wherein said first major surface of said contained product has a predetermined surface area and said sheath has a surface area which is greater than said predetermined surface area.

8. The dispensing aid of claim 1 wherein said first major surface of said contained product has a predetermined surface area and said sheath has a surface area which is equal to said predetermined surface area.

9. The dispensing aid of claim 1 wherein said first major surface of said contained product has a predetermined surface area and said sheath has a surface area which is less than said predetermined surface area.

10. A dispensing aid for facilitating removal of an individual product from a compressed package, comprising:
    a) a plurality of products arranged in a row within said compressed package, each of said products having a first major surface and a second major surface, said first major surface aligned opposite to said second major surface, and said first major surface of a product to a major surface of an adjacent product having an average coefficient of friction value;
    b) an opening formed in a wall of said compressed package, said opening being aligned perpendicular to said first major surface of at least one of said products, and said opening being of sufficient size to allow said products to be individually withdrawn such that, as a product is removed from said compressed package, said first major surface of an exiting product will move parallel to an adjacent product; and c) a plurality of sheaths each having an open end and each being sized to contain one of said products to be withdrawn from said compressed package, each of said sheaths to an adjacent sheath having an average coefficient of friction value which is at least 2 times lower than said average coefficient of friction value of said first major surface of a product to a major surface of an adjacent product, whereby each of said sheaths reduces the force needed to remove said contained product from said compressed package.

11. The dispensing aid of claim 10 wherein at least 50% of said products within said compressed package are each contained in a sheath.

12. The dispensing aid of claim 11 wherein at least 75% of said products within said compressed package are each contained in a sheath.

13. The dispensing aid of claim 10 wherein said sheath is constructed from a polymeric material.

14. The dispensing aid of claim 10 wherein said first major surface of each of said products within said compressed package has a predetermined surface area, and each of said sheaths has a surface area which ranges from between about 25% to about 120% of said predetermined surface area.

15. The dispensing aid of claim 10 wherein said first major surface of each of said products within said compressed package is folded into a generally rectangular configuration and each of said sheaths has a generally rectangular configuration.

16. A dispensing aid for facilitating removal of an individual product from a compressed package, comprising:

a) a plurality of products arranged in a row within said compressed package, each of said products having a first major surface and a second major surface, said first major surface aligned opposite to said second major surface, and said first major surface of a product to a major surface of an adjacent product having an average coefficient of friction value;

b) an opening formed in a wall of said compressed package, said opening being aligned perpendicular to said first major surface of at least one of said products, and said opening being of sufficient size to allow said products to be individually withdrawn, such that as a product is removed from said compressed package, said first major surface of an exiting product will move parallel to an adjacent product; and c) a plurality of sheaths each having an open end and each being sized to contain one of said products to be withdrawn from said compressed package, each of said sheaths to an adjacent sheath having an average coefficient of friction value which is at least 3 times lower than said average coefficient of friction value of said first major surface of a product to a major surface of an adjacent product, whereby each of said sheaths reduces the force needed to remove said contained product from said compressed package.

17. The dispensing aid of claim 16 wherein each of said products has a height dimension and each of said sheaths has a height dimension which is greater than said height dimension of said contained product.

18. The dispensing aid of claim 16 wherein each of said sheaths is formed from a low density polymeric film.

19. The dispensing aid of claim 18 wherein each of said sheaths is formed from a blown film.

20. The dispensing aid of claim 18 wherein each of said sheaths is formed from a cast film.

21. The dispensing aid of claim 18 wherein said sheath is used to contain a soiled absorbent article once said product has been removed therefrom.

\* \* \* \* \*